US011328416B2

(12) United States Patent
Zareian et al.

(10) Patent No.: US 11,328,416 B2
(45) Date of Patent: May 10, 2022

(54) METHOD FOR IDENTIFICATION AND QUANTIFICATION OF TISSUE CALCIFICATION

(71) Applicant: The Regents of the University of California, Oakland, CA (US)

(72) Inventors: Ramin Zareian, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 103 days.

(21) Appl. No.: 16/746,135

(22) Filed: Jan. 17, 2020

(65) Prior Publication Data
US 2020/0234440 A1 Jul. 23, 2020

Related U.S. Application Data

(60) Provisional application No. 62/794,358, filed on Jan. 18, 2019.

(51) Int. Cl.
*G06K 9/00* (2022.01)
*G06T 7/00* (2017.01)
(Continued)

(52) U.S. Cl.
CPC .............. *G06T 7/0012* (2013.01); *G01N 1/30* (2013.01); *G06N 20/00* (2019.01); *G06T 7/62* (2017.01);
(Continued)

(58) Field of Classification Search
CPC .................................................. G06T 7/0012
See application file for complete search history.

(56) References Cited

U.S. PATENT DOCUMENTS

| 2011/0019886 A1* | 1/2011 | Mizuno | G06T 7/0014 |
| | | | 382/128 |
| 2013/0243288 A1* | 9/2013 | Goto | G06K 9/6204 |
| | | | 382/128 |

(Continued)

OTHER PUBLICATIONS

Leon MB et al. "Transcatheter or Surgical Aortic-Valve Replacement in Intermediate-Risk Patients" N Engl J Med 2016; 374:1609-1620.

(Continued)

*Primary Examiner* — Oneal R Mistry
(74) *Attorney, Agent, or Firm* — Nguyen Tarbet LLC

(57) ABSTRACT

A method of identifying and quantifying calcified regions of a tissue including obtaining an image of a cross-section of the tissue, wherein the image distinguishes between calcified regions and non-calcified regions of the cross-section of the tissue. Also disclosed are methods of detecting a change in size of a calcified region of a tissue over time including identifying and quantifying a first size of the calcified region of the tissue at a first time, identifying and quantifying a second size of the corresponding calcified region of the tissue at a second time, and detecting a change in size between the first and second size of the calcified region of the tissue in the image of a cross-section of the tissue. Some aspects relate to computer software program configured to construct a panoramic image from partial images, quantify RGB values for each pixel in the panoramic image, and calculate the total pixels of calcified and uncalcified regions and a calcification ratio.

18 Claims, 14 Drawing Sheets

(51) Int. Cl.
  *G01N 1/30* (2006.01)
  *G06N 20/00* (2019.01)
  *G06T 7/62* (2017.01)
(52) U.S. Cl.
  CPC .............. *G06T 2207/10024* (2013.01); *G06T 2207/10081* (2013.01); *G06T 2207/30048* (2013.01); *G06T 2207/30052* (2013.01)

(56) References Cited

U.S. PATENT DOCUMENTS

| | | | | |
|---|---|---|---|---|
| 2014/0350350 | A1* | 11/2014 | Imagawa | A61B 6/504 600/300 |
| 2016/0045316 | A1* | 2/2016 | Braido | A61B 5/0215 623/2.38 |
| 2017/0296055 | A1* | 10/2017 | Gardner | G01N 21/314 |
| 2018/0245243 | A1* | 8/2018 | Krieger | A61F 2/06 |
| 2018/0300875 | A1* | 10/2018 | Imasugi | G06T 5/50 |
| 2020/0226422 | A1* | 7/2020 | Li | G06N 3/08 |

OTHER PUBLICATIONS

Dvir D et al. Standardized Definition of Structural Valve Degeneration for Surgical and Transcatheter Bioprosthetic Aortic Valves Circulation 2018; 137:388-399.
Kheradvar A et al. "Emerging Trends in Heart Valve Engineering: Part II. Novel and Standard Technologies for Aortic Valve Replacement" Ann Biomed Eng 2015; 43:844-857.
Zegdi R et al. "Evidence of leaflet injury during percutaneous aortic valve deployment" Eur J Cardiothorac Surg 2011; 40:257-260.
De Buhr W et al. "Impairment of pericardial leaflet structure from balloon-expanded valved stents" J Thorac Cardiovasc Surg 2012; 143:1417-1421.
Kiefer P et al. "Crimping May Affect the Durability of Transcatheter Valves: An Experimental Analysis" Ann Thorac Surg 2011; 92:155-160.
Ong SH et al. "Early calcific degeneration of a CoreValve transcatheter aortic bioprosthesis" Eur Heart J 2012; 33:586.
Richardt D et al. "Two Cases of Heart Failure after Implantation of a CoreValve Prosthesis" N Engl J Med 2015;372:1079-1081.
Van Steenberghe M et al. "Early transcatheter aortic valve degeneration in the young" Int J Cardiol 2016;222:786-787.
Harbaoui B et al. "Early Edwards Sapien Valve Degeneration After Transcatheter Aortic Valve Replacement" JACC Cardiovasc Interv 2016; 9:198-199.
Pascual I et al. "Degenerative Pattern of a Percutaneous Aortic Valve" Rev Esp Cardiol (Engl Ed) 2017; 70:772.
Webb JG et al. "Is Transcatheter Aortic Valve Replacement a Durable Therapeutic Strategy?" JACC Cardiovasc Interv 2015; 8:1092-1094.

Deutsch M-A et al. "Structural Valve Deterioration 4 Years After Transcatheter Aortic Valve Replacement" Circulation 2015; 131:682-685.
Arora S et al. "Early transcatheter valve prosthesis degeneration and future ramifications" Cardiovasc Diagn Ther 2017; 7:1-3.
Makkar RR et al. "Transcatheter Aortic Valve Thrombosis" JACC Cardiovasc Interv 2017; 10:698-700.
Barannyk O et al. "A correlation between long-term in vitro dynamic calcification and abnormal flow patterns past bioprosthetic heart valves" J Biol Phys 2017; 43:279-296.
Kapolos J. et al. "Model Experimental System for Investigation of Heart Valve Calcification In Vitro" J Biomed Mater Res 1997; 38:183-190.
Krings M. et al. "Development of a new combined test setup for accelerated dynamic pH-controlled in vitro calcification of porcine heart valves" Int J Artif Organs 2009; 32:794-801.
Tertti R. et al. "Comparison of calcium phosphate product values using measurement of plasma total calcium and serum ionized calcium" Hemodialysis Int 2007; 11:411-416.
Mann HB et al. "On a test of whether one or two random variables is stochastically larger than the other" Ann Math Statist 1947; 18: 50-60.
Alavi SH et al. "The Effects of Transcatheter Valve Crimping on Pericardial Leaflets" Ann Thorac Surg 2014;97:1260-1266.
Otto CM. et al. "Calcification of bicuspid aortic valves" Heart 2002; 88:321-322.
Cheng CL et al. "Ex vivo assessment of valve thickness/calcification of patients with calcific aortic stenosis in relation to in vivo clinical outcomes" J Mech Behav Biomed Mater 2017; 74:324-332.
Foroutan F. et al. "Structural valve deterioration after transcatheter aortic valve implantation" Heart 2017; 103:1899-1905.
Dasi LP. et al. "On the Mechanics of Transcatheter Aortic Valve Replacement" Ann Biomed Eng 2017; 45:310-331.
Delogne C. et al. "Characterization of the calcification of cardiac valve bioprostheses by environmental scanning electron microscopy and vibrational spectroscopy" J Microsc 2007; 228:62-77.
Schoen FJ et al. "Calcification of bovine pericardium used in cardiac valve bioprostheses" Am J Pathol 1986; 123:134-145.
Bertazzo S. et al. "Nano-analytical electron microscopy reveals fundamental insights into human cardiovascular tissue calcification" Nature Mater 2013; 12: 576-583.
Schoen FJ et al. "Calcification of Tissue Heart Valve Substitutes: Progress Toward Understanding and Prevention" Ann Thorac Surg 2005; 79: 1072-1080.
Khoffi F. et al. "Transcatheter fiber heart valve: Effect of crimping on material performances" J Biomed Mater Res B Res 2015; 103:1488-1497.
Bush CH, et al. "Mineralization in Musculoskeletal Leiomyosarcoma: Radiologic-Pathologic Correlation" AJR. 2003; 180:109-113.
Zareian, Ramin, et al., "Effect of stent crimping on calcification of transcatheter aortic valves," (2019 Interactive CardioVascular and Thoracic Surgery, 29(1): 64-73.

* cited by examiner

METHOD FOR IDENTIFICATION AND QUANTIFICATION OF TISSUE CALCIFICATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Identification and quantification of calcified regions of a tissue stained by computed tomography (CT) imaging or by a calcification-specific stain. An understanding of the effect of stent crimping on calcification provides a basis for improving the durability of transcatheter heart valves.

Background

Transcatheter aortic valve replacement (TAVR) is an emerging technology with great promise for revolutionizing the treatment of valvular heart disease. Short-term data suggests that TAVR in patients with severe aortic stenosis who were unsuitable candidates for surgery significantly reduces all-cause mortality, the composite endpoint of all-cause death, or repeat hospitalization and cardiac symptoms, compared to standard therapy, with a comparable incidence of stroke and major vascular events. More recent studies suggest that TAVR will provide patients with intermediate risk for traditional surgery a similar outcome with respect to the primary endpoint of death or disabling stroke at 2 years (Leon M B, et al. New England Journal of Medicine 2016; 3 74:1609-20). However, TAVR has only been widely available since 2007, and thus, its long-term durability is not yet known (Dvir D, et al. Circulation 2018; 137:388).

Transcatheter heart valves share some characteristics with bioprosthetic surgical valves, but also have many unique properties (Kheradvar A, et al. Annals of Biomedical Engineering 314 2015; 43:844-57). The most important similarity is their leaflet, which is made mainly of pericardial tissue. Alternatively, their major difference is the housing of transcatheter heart valves' leaflets within a stent, exposure to stent-crimping before implantation and non-optimal expansion, which may lead to unfavorable interaction with the native aortic root. These valves' designs leave the pericardial leaflets crimped within a compressed stent during delivery until implantation, which takes about 5 to 10 minutes. Doing so, exposes the stented leaflets to a level of stress that is not applied to surgical bioprosthetic valves. Currently, only little quantitative data is available on the basis of which to assess the damage that results from stent-crimping (Zegdi R, et al. European Journal of Cardio-Thoracic Surgery 317 2011; 40:257-60; de Buhr W, et al. Journal of Thoracic and Cardiovascular Surgery 2012; and Kiefer P, et al. The Annals of thoracic surgery 2011; 92:155-60). More recently, several clinical studies have reported premature degeneration of the transcatheter heart valves (Ong S H, et al. European Heart Journal 2012; 33:586; Richardt D, et al. New England Journal of Medicine 328 2015; 372:1079-81; van Steenberghe M, et al. Cardiology; 222:786-87; Harbaoui B, et al. JACC: Cardiovascular Interventions 2016; 9:198; Pascual I, et al. Rev Esp Cardiol (Engl Ed) 2017; S1885-5857:30048-8; Webb J G, and Dvir D. JACC: Cardiovascular Interventions 2015; 8:1092; Deutsch M-A, et al. Circulation 2015; 131:682; and Arora S, et al. Therapy 2017; 7:1-3). However, no quantitative study has yet convincingly shown that stent-crimp-induced damage to the leaflets is indeed the reason for premature structural degeneration and calcification. Further, these areas could be a nidus for valve leaflet thrombosis that is known to be more common in TAVR (Makkar R R and Chakravarty T. JACC: Cardiovascular Interventions 2017; 10:698-700).

Mineralization within soft-tissue masses can result from calcification (Bush C H, et al. AJR. 2003; 180:109-113) and produces the appearance of high-density material on radiographs or CT scans. The pattern and morphologic characteristics of mineralization can be a clue to a soft-tissue mass's cause, and hence, suggest a histologic diagnosis.

SUMMARY

We have tested the effect of stent-crimp on premature calcification.

Some aspects relate to a method of identifying and quantifying calcified regions of a tissue including obtaining an image of a cross-section of the tissue, wherein the image distinguishes between calcified regions and non-calcified regions of the cross-section of the tissue.

In some examples, the method uses computed tomography (CT) to obtain the image of the cross-section of the tissue, wherein calcified regions in the tissue are distinguished by appearance of high-density material in a CT cross-sectional image.

Some examples include non-invasively obtaining the CT cross-sectional image of the tissue in a living subject.

Some examples include histologically staining the cross-section of the tissue by a calcification-specific stain and generating a dual color image to detect calcified and non-calcified regions of the cross-section of the tissue.

Some examples include calculating a calcification ratio based on the following formula:

$$\text{Calcification Ratio} = \frac{\text{total pixels of the calcified region}}{\text{total pixels of the calcified and uncalcified regions}} \times (100).$$

In some examples, the image is of a native or prosthetic heart valve.

In some examples, the native or prosthetic heart valve comprises pericardial tissue.

In some examples the native or prosthetic heart valve comprises xenogeneic heart valve tissue.

In some examples the native or prosthetic heart valve comprises a synthetic polymeric material.

In some examples, the tissue is stained by von Kossa staining.

In some examples, a panoramic image is constructed from partial images captured from the tissue.

In some examples, the calcified region is in a subject and wherein the method further includes treating the subject with a medical procedure to reduce one or more of the calcified regions.

Some aspects relate to a method of detecting a change in size of a calcified region of a tissue over time including:
(a) using the method according to claim 1 to:
  (i) identify and quantify a first size of the calcified region of the tissue at a first time, and (ii) identify and quantify a second size of the corresponding calcified region of the tissue at a second time, and (b) detecting a change in size between the first and second size of the calcified region of the tissue in the image of a cross-section of the tissue.

In some examples, the calcified region is in a subject and the method further includes treating the subject with a medical procedure to reduce the calcified tissue if the second size is increased compared to the first size.

In some examples, the calcified region of tissue is associated with a transcatheter heart valve implanted in a subject.

In some examples, the calcified region increases thickness of leaflets in the transcatheter heart valve.

In some examples, the calcified region produces one or more calcium nodules on a heart valve leaflet.

In some examples, the calcified region is located at valve sutures or at valve posts, which are under high mechanical stress.

In some examples, the sizes or ratios of the calcified regions and non-calcified regions of the cross-section of the tissue are calculated by a computer software program configured to:

construct a panoramic image from partial images, quantify RGB values for each pixel in the panoramic image, and calculate the total pixels of calcified and uncalcified regions and a calcification ratio.

Some aspects relate to computer software program configured to:

construct a panoramic image from partial images, quantify RGB values for each pixel in the panoramic image, and calculate the total pixels of calcified and uncalcified regions and a calcification ratio.

$$\text{Calcification Ratio} = \frac{\text{total pixels of the calcified region}}{\text{total pixels of the calcified and uncalcified regions}} \times (100).$$

Figure 2:
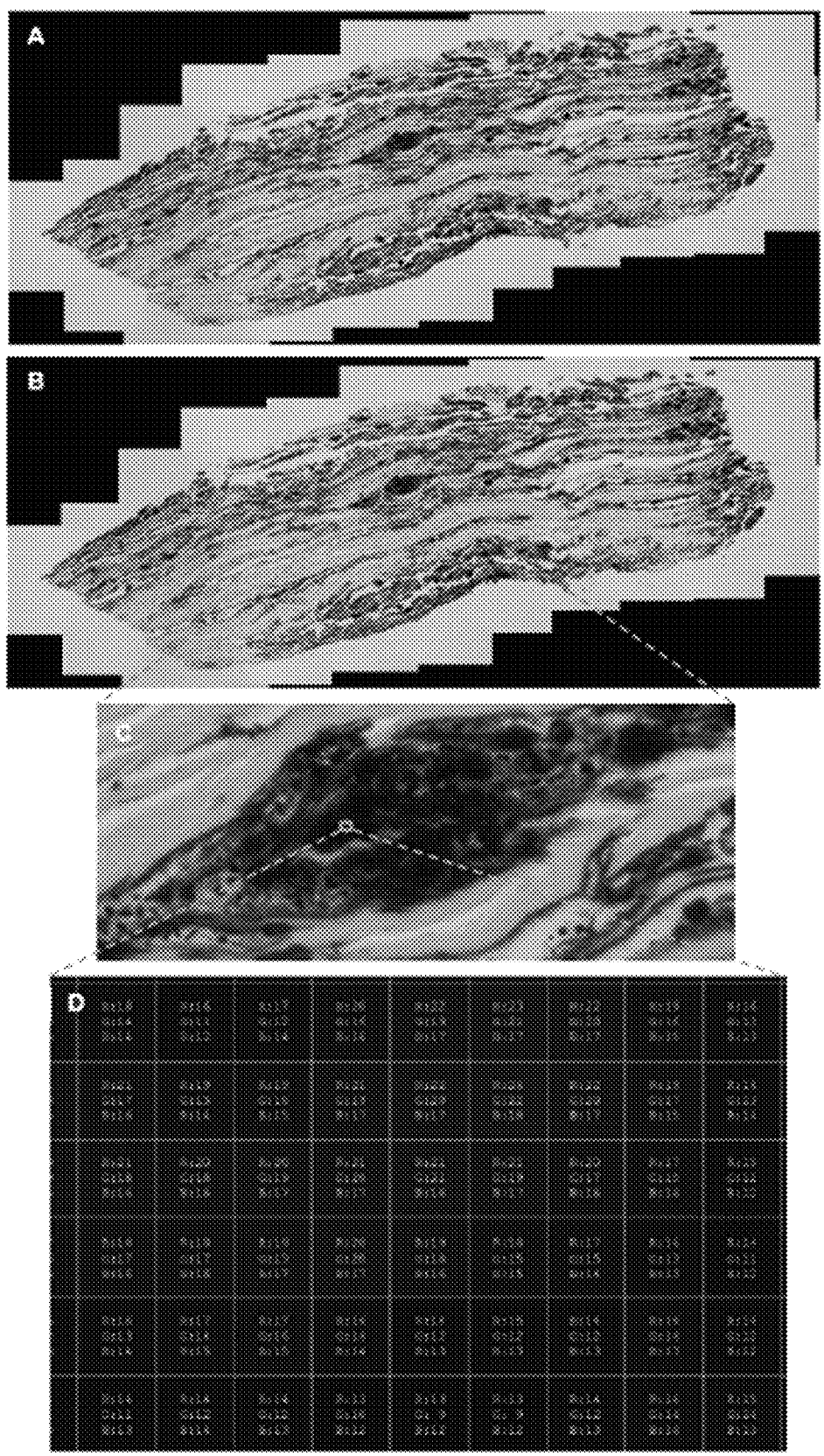
FIG. 2: (A) the large image constructed with 41 partial images, (B) the large image saved in 8-bit and TIFF format, (C) a magnified view of the calcified tissue in the 8-bit image, (D) the quantified image of the calcified tissue in RGB values.
Figure 4:
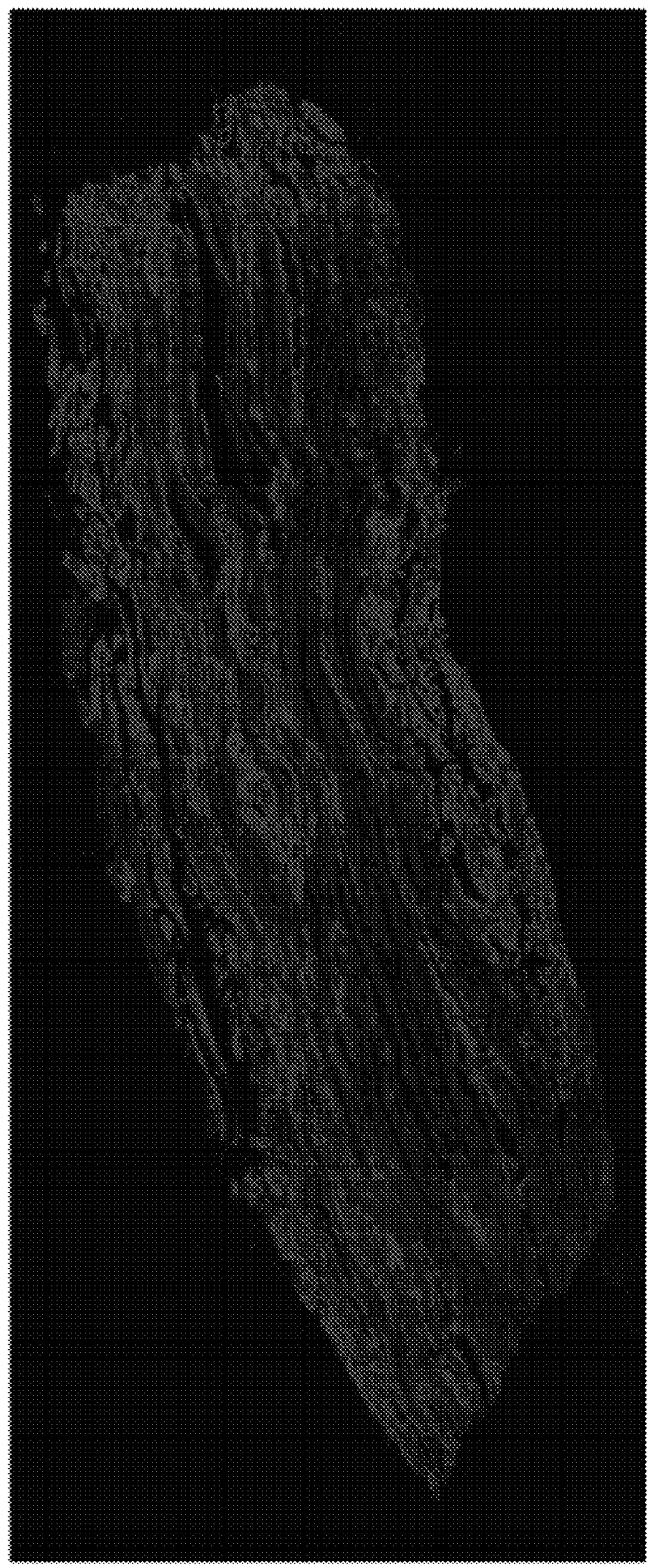

FIG. 4 shows the dual color image reconstructed from the panoramic image shown in FIG. 2. The dark gray and light gray regions demonstrate the uncalcified and calcified regions in the image.

Figure 5:
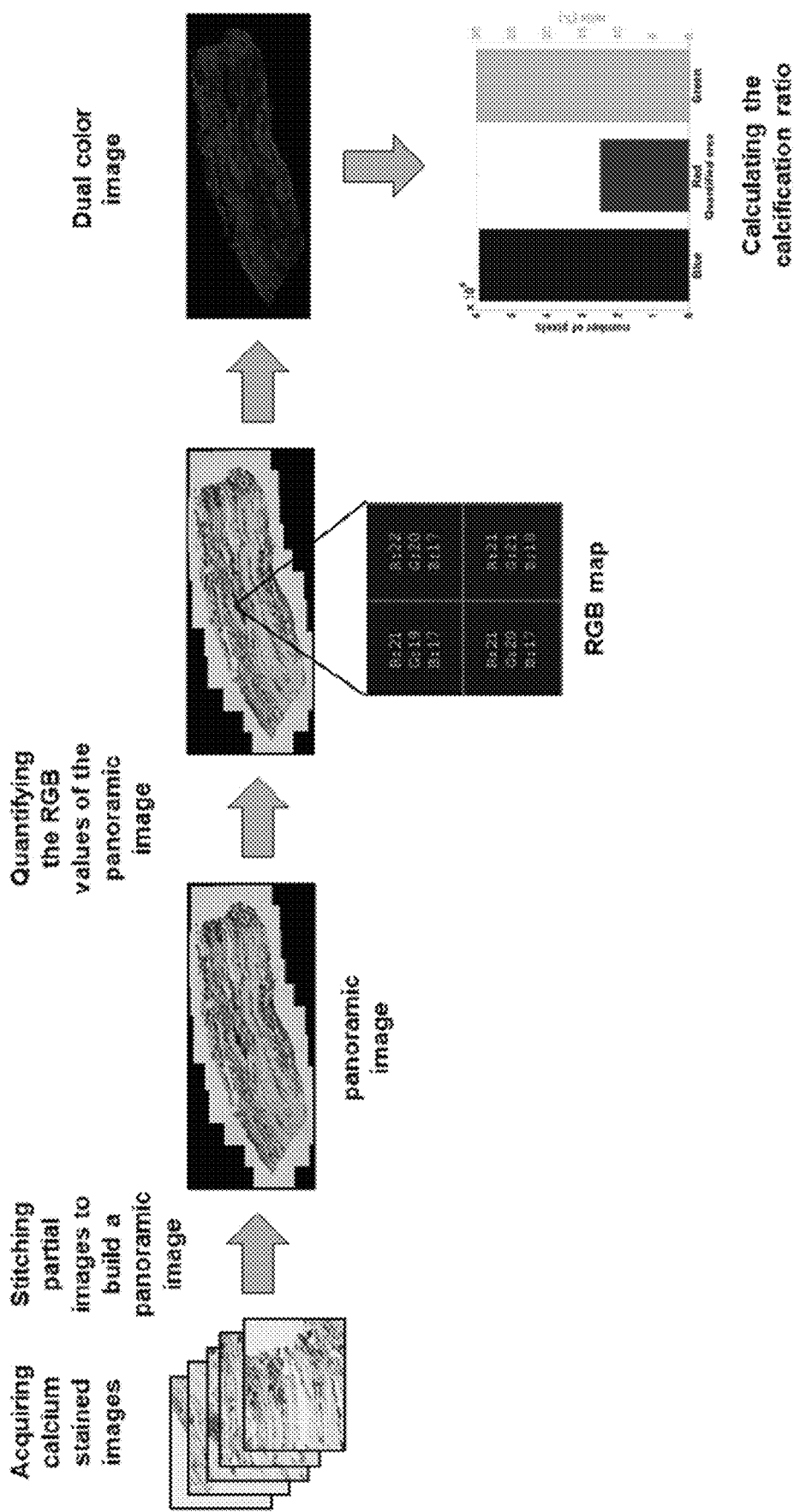

FIG. 5. Process diagram showing steps from acquisition of calcium stained images through calculation of calcification ratios.

Figure 6:
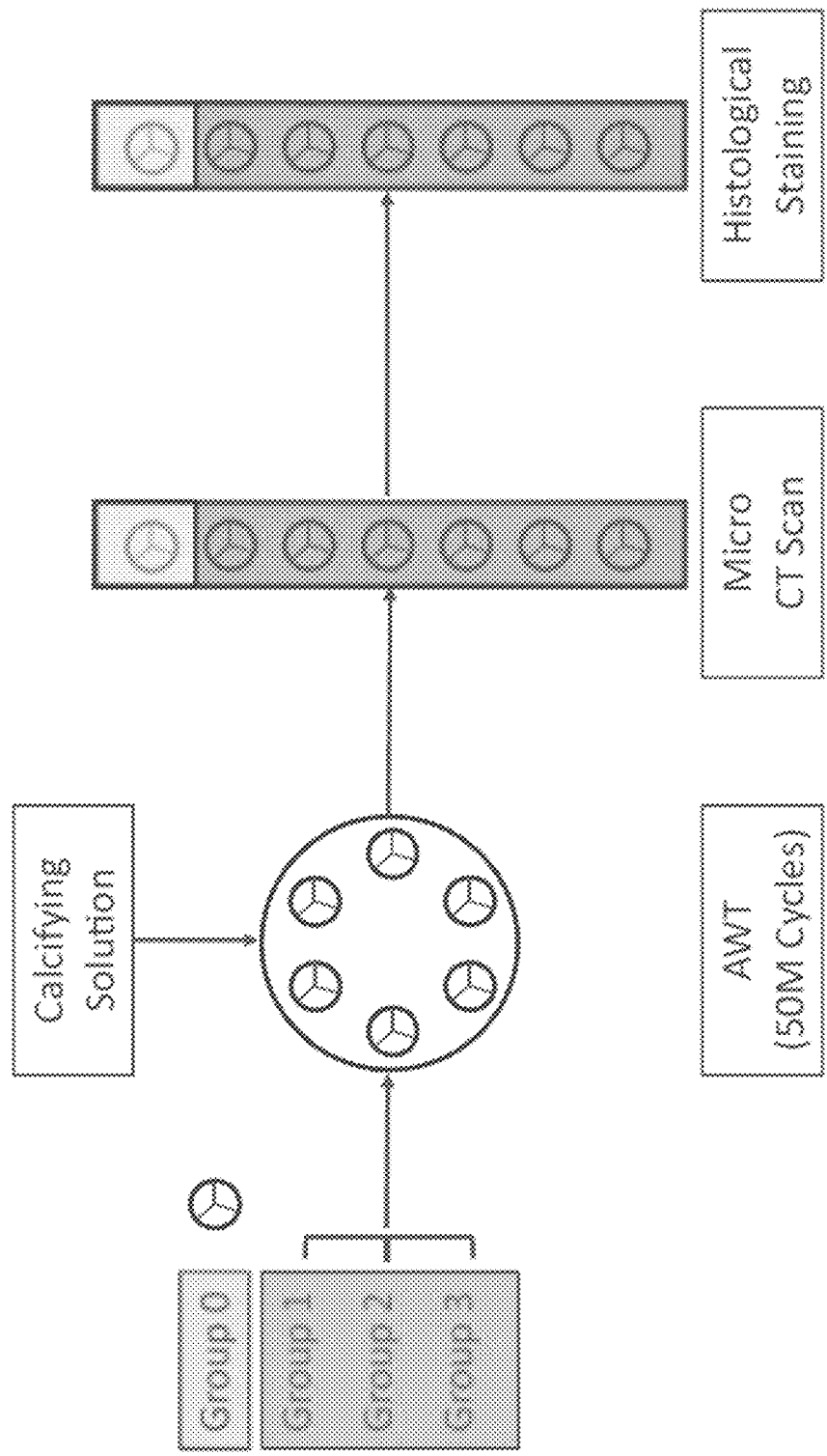

FIG. 6. Schematics of the experiments to quantify and compare the durability of heart valves. The diagram shows the 6 valves in groups 1-3 that are tested for durability in the presence of a calcifying solution and then compared with alike control valve in group 0 by microcomputed tomography scans and histological staining. Group 0: control; uncrimped (N=1); group 1: uncrimped calcified (N=2); group 2: crimped at 18-Fr calcified (N=2); and group 3: crimped at 14-Fr and calcified (N=2). AWT: accelerated wear test; CT: computed tomography.

Figure 7:
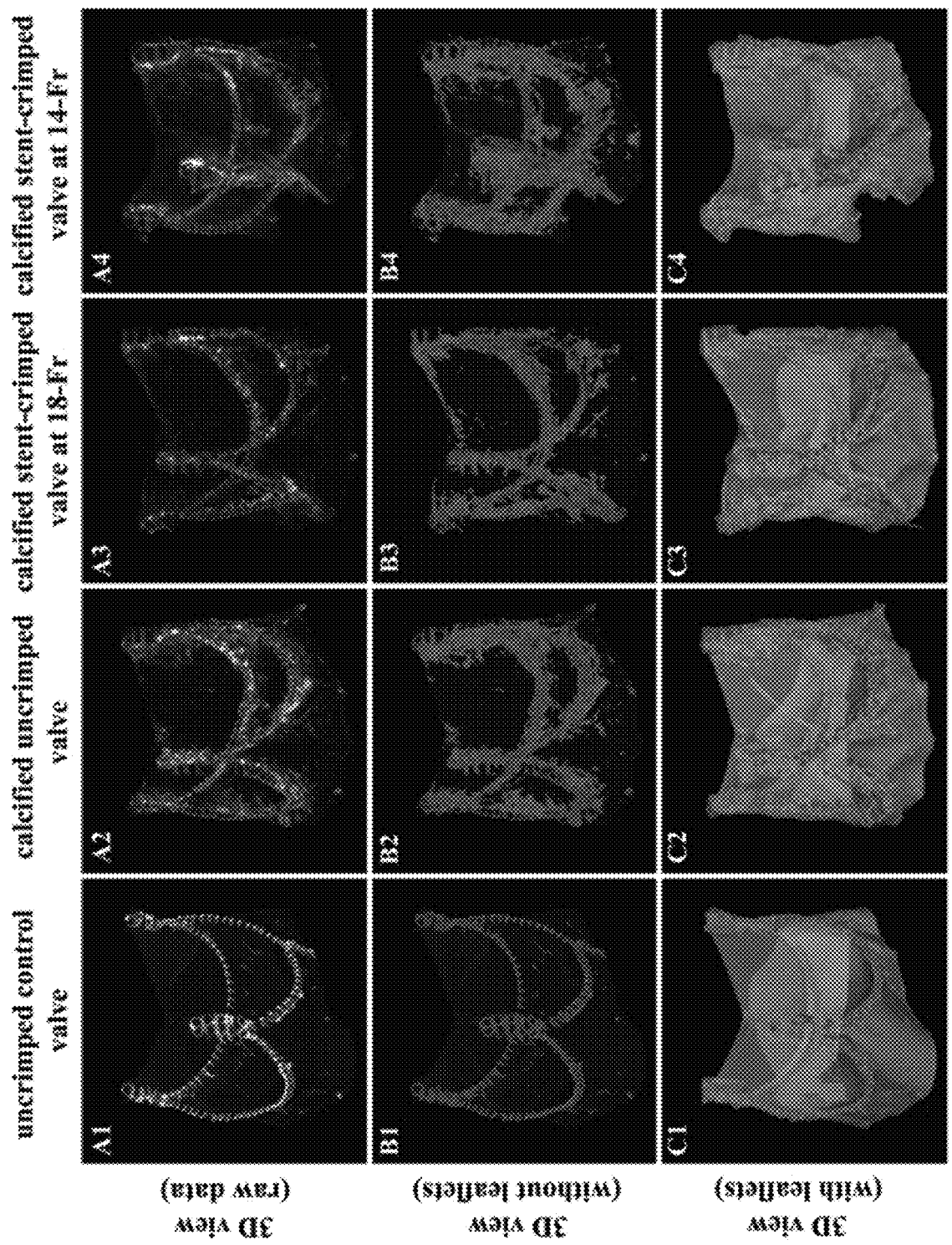

FIG. 7. Comparison between stent-crimped and uncrimped valves after 50 million cycles of the accelerated wear test. The raw data representing 3D microcomputed tomographic (micro-CT) scans of an uncrimped control valve (A1); a calcified uncrimped valve (A2); a calcified stent-crimped valve at 18-Fr (A3); and a calcified stent-crimped valve at 14-Fr (A4). The 3D view of the quantified micro-CT images of an uncrimped control valve (B1), a calcified uncrimped valve (B2), a calcified stent-crimped valve at 18-Fr (B3) and calcified stent-crimped valve at 14-Fr (B4) showing the valve's sutures and calcified regions in dark gray and light gray, respectively. The 3D views of the quantified micro-CT images of an uncrimped control valve (C1), a calcified uncrimped valve (C2), a calcified stent-crimped valve at 18-Fr (C3) and calcified stent-crimped valve at 14-Fr (C4) along with the valve's leaflets. 3D: 3-dimensional.

Figure 8:
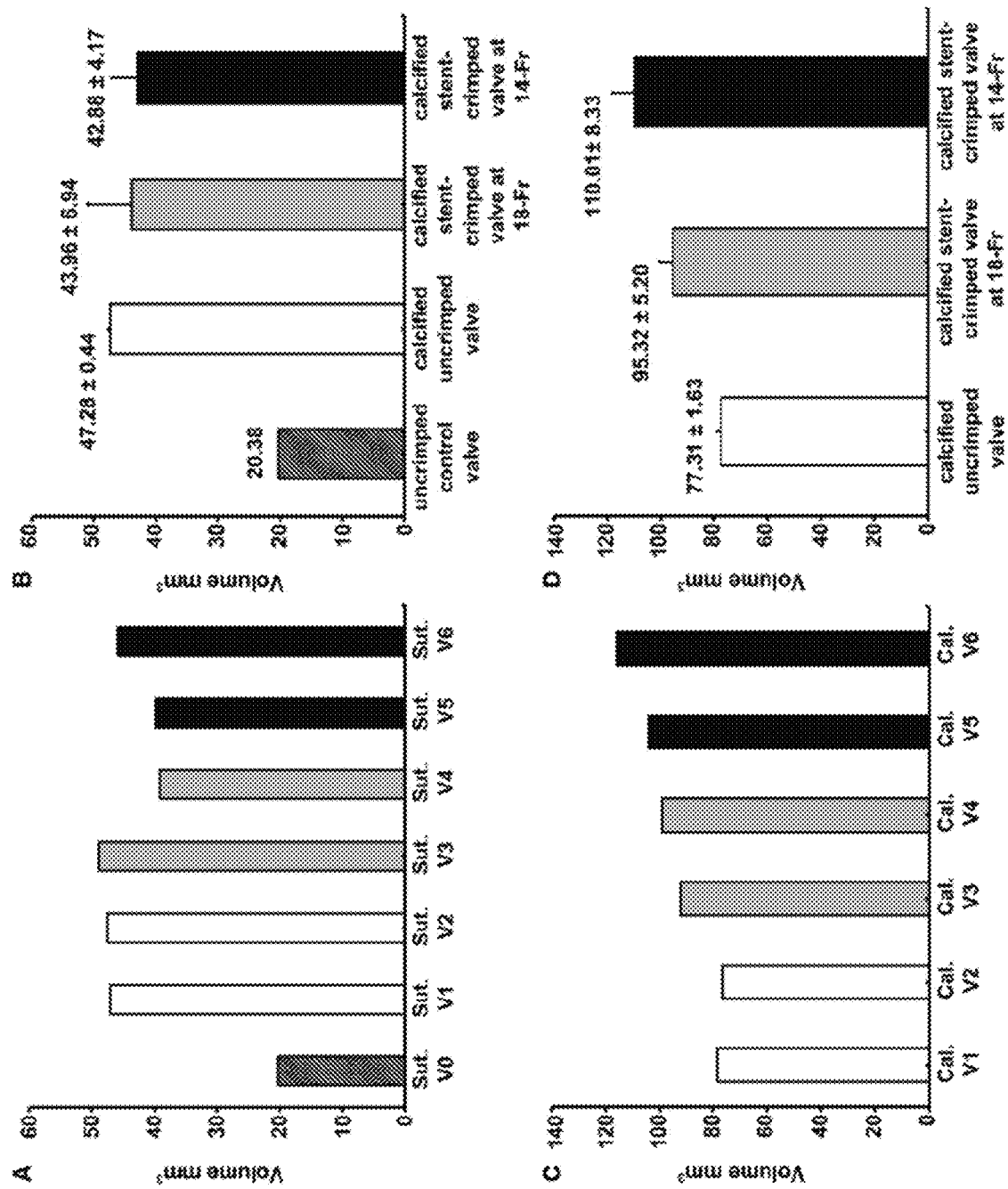

FIG. 8. Quantification of calcified regions using microcomputed tomographic scanning. (A) Total suture volume was quantified for each valve. (B) The quantified suture volume for each group is shown as the mean±standard deviation. (C) Total calcification volume is quantified for each valve. (D) The quantified calcification volume for each group is shown as mean±standard deviation. Cal: calcification; Sut: suture; V0: (valve 0) uncrimped control; V1: (valve 1) calcified uncrimped; V2: (valve 2) calcified uncrimped; V3: (valve 3) calcified crimped valve at 18-Fr; V4: (valve 4) calcified crimped valve at 18-Fr; V5: (valve 5) calcified crimped valve at 14-Fr; V6: (valve 6) calcified crimped valve at 14-Fr.

Figure 9:
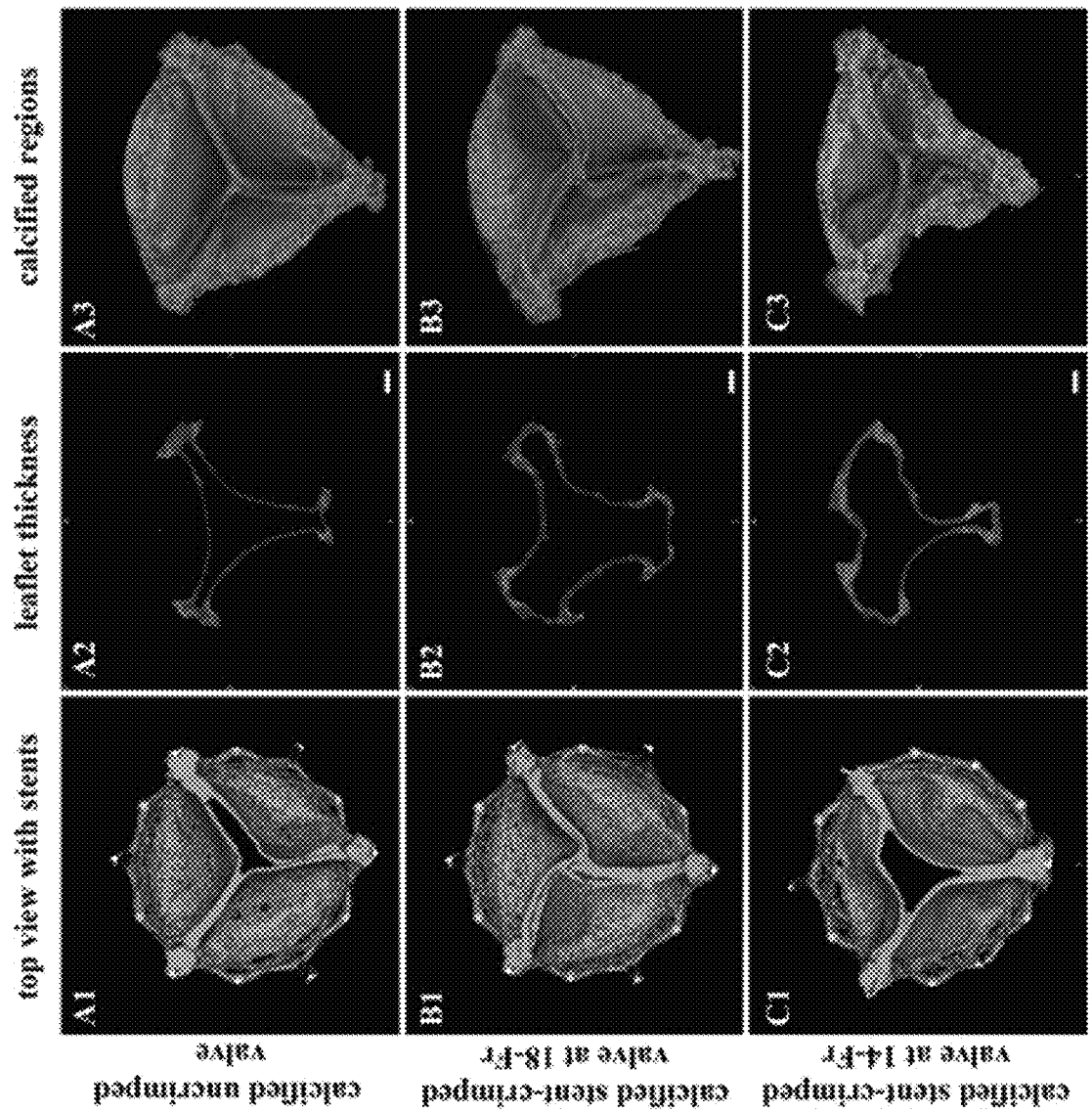

FIG. 9. Association between the thickness of the leaflets and calcification. Microcomputed tomographic (micro-CT) views of a calcified uncrimped valve (A1-3); a calcified stent-crimped valve at 18-Fr (B1-3); and a calcified stent-crimped valve at 14-Fr (C1-3). A1, B1 and C1 show the top views of the valves; A2, B2 and C2 show how valves are quantified at each slice from the z-stack. A3, B3 and C3 show the fully analyzed CT images of the valve, differentiating between sutures (dark gray) and calcification regions (light gray), respectively. Scale bars are 2.5 mm.

Figure 10:
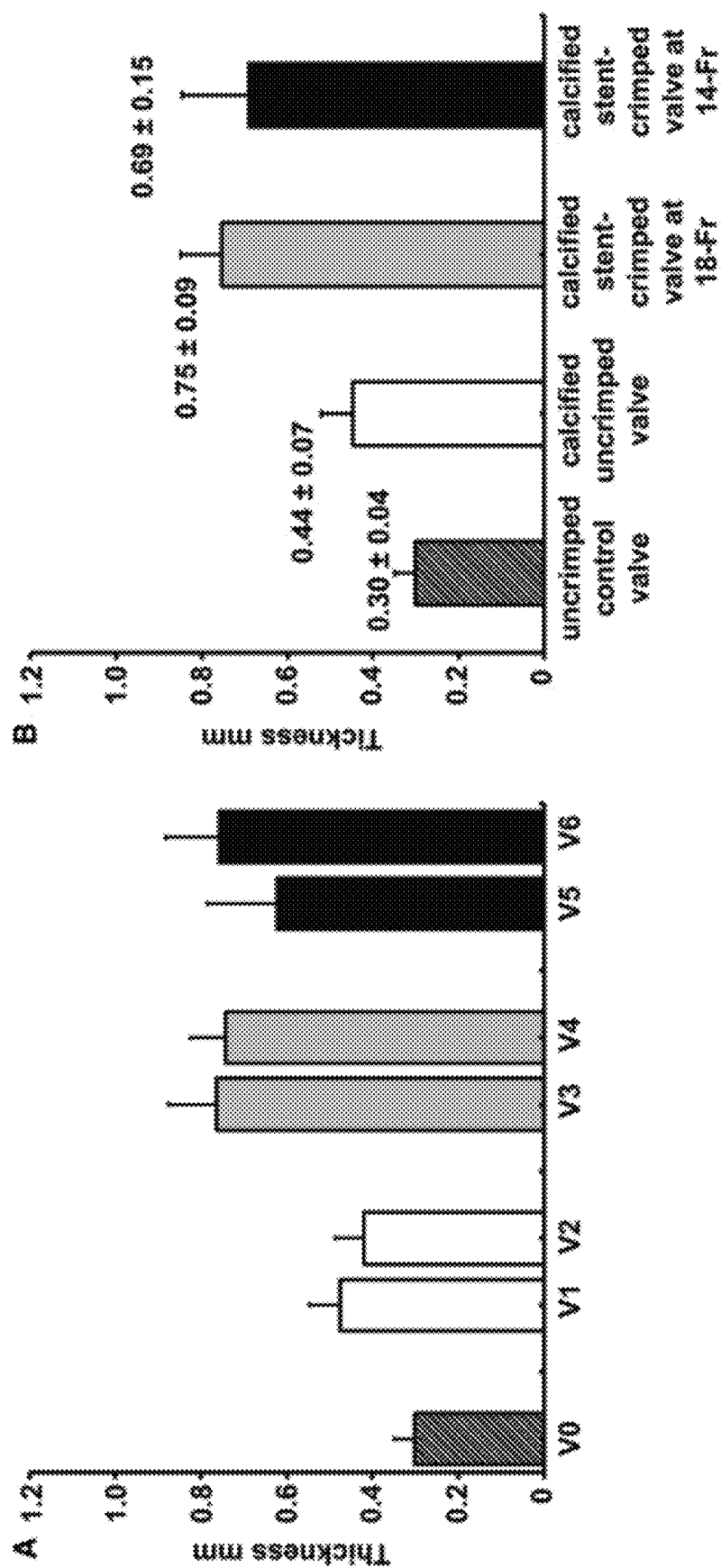

FIG. 10. Valve thickness measurement using microcomputed tomographic scanning. (A) The measured thickness of the leaflets for each studied valve. (B) The measured thicknesses of the leaflets for each studied group. The measured thicknesses of the leaflets are shown as the mean±standard deviation. V0: (valve 0) uncrimped control; V1: (valve 1) calcified uncrimped; V2: (valve 2) calcified uncrimped; V3: (valve 3) calcified stent-crimped valve at 18-Fr; V4: (valve 4) calcified stent-crimped valve at 18-Fr; V5: (valve 5) calcified stent-crimped valve at 14-Fr; V6: (valve 6) calcified stent-crimped valve at 14-Fr.

Figure 11:
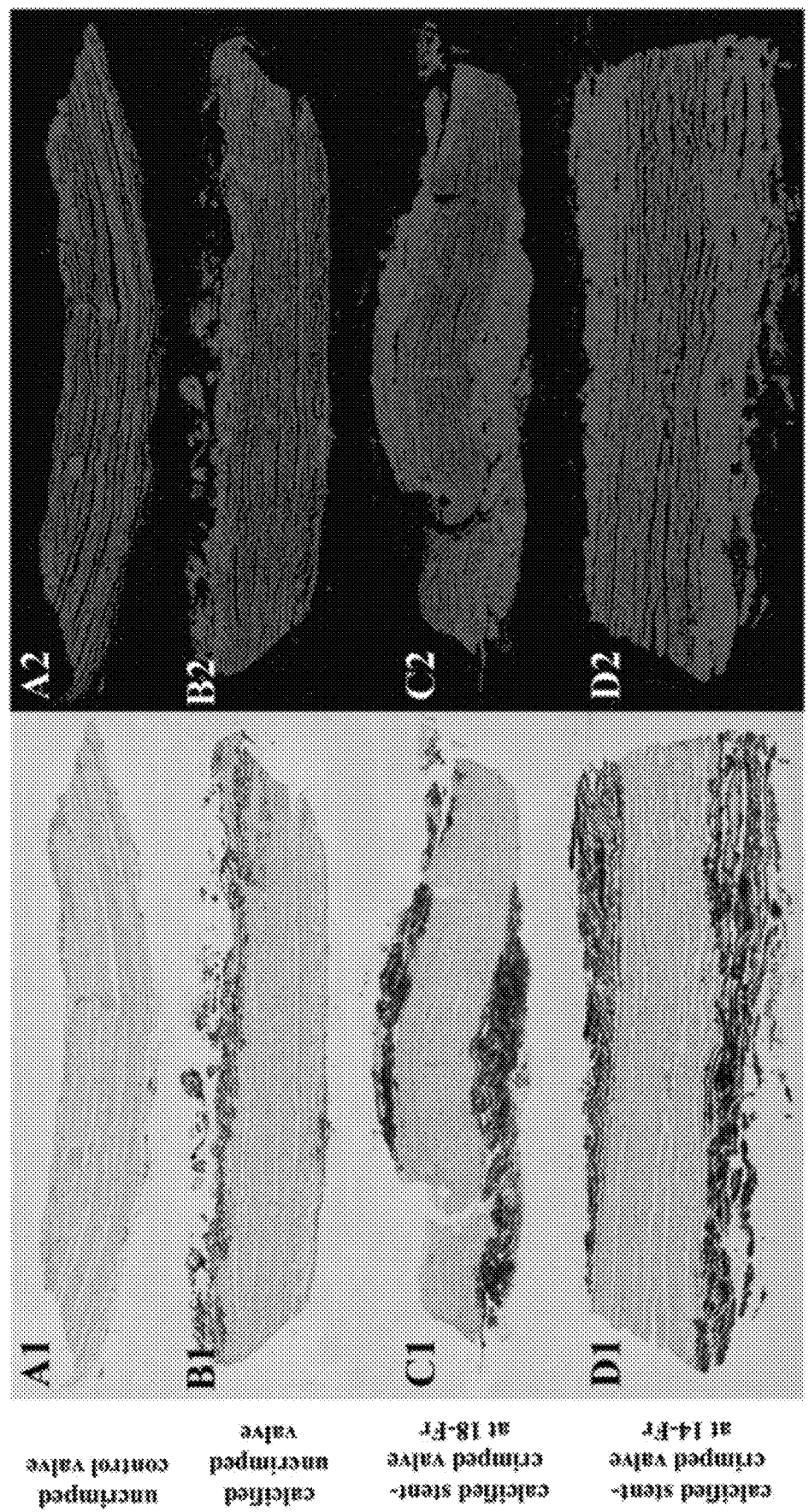

FIG. 11. Von Kossa staining for quantifying calcification. The panels compare Von Kossa staining of representative samples of 4 different studied valve groups along with their computer-generated RGB map: a sample from the uncrimped control valve (A1-2); from a calcified uncrimped valve (B1-2); from a calcified stent-crimped valve at 18-Fr (C1-2); and from a calcified stent-crimped valve at 14-Fr (D1-2). A1, B1, C1 and D1 are Von Kossa-stained cross-sections of 4 different valves. Black regions demonstrate the calcification. A2, B2, C2 and D2 are computer-generated RGB maps quantified by an in-house MATLAB routine. Dark gray and light gray represent uncalcified and calcified regions, respectively. RGB: red, green and blue.

Figure 12:
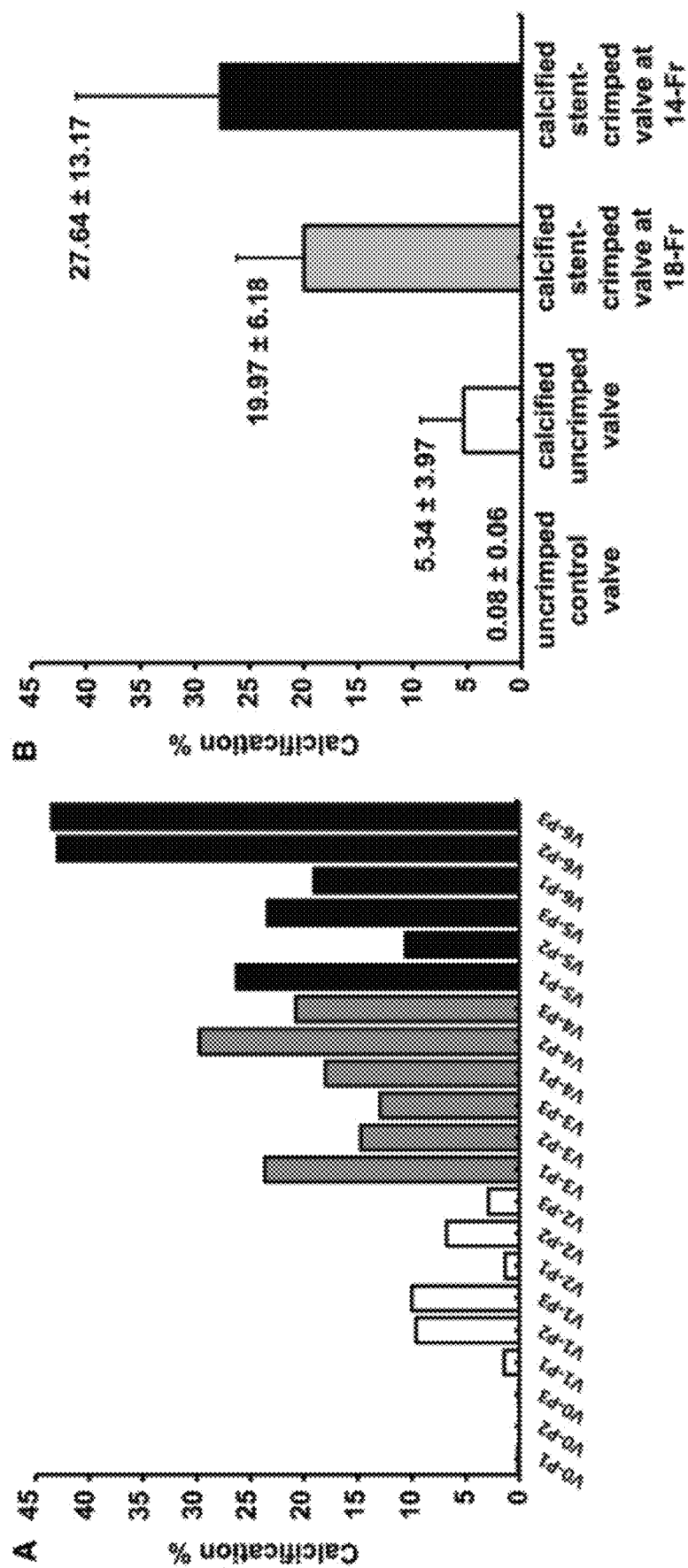

FIG. 12. Quantification of calcified regions using histopathological analysis. (A) Total calcification ratio in terms of percentage quantified for each valve's post according to the computer analyses of the Von Kossa staining. (B) The average calcification in terms of percentage for all the valves' posts in each studied group is shown as mean±standard deviation. V0: (valve 0) uncrimped control; V1: (valve 1) calcified uncrimped; V2: (valve 2) calcified uncrimped; V3: (valve 3) calcified stent-crimped valve at 18-Fr; V4: (valve 4) calcified stent-crimped valve at 18-Fr; V5: (valve 5) calcified stent-crimped valve at 14-Fr; V6: (valve 6) calcified stent-crimped valve at 14-Fr; P1, P2 and P3 denote valve posts 1, 2 and 3, respectively. Three punch biopsies were taken from each valve, adjacent to the valve's post.

Figure 13:
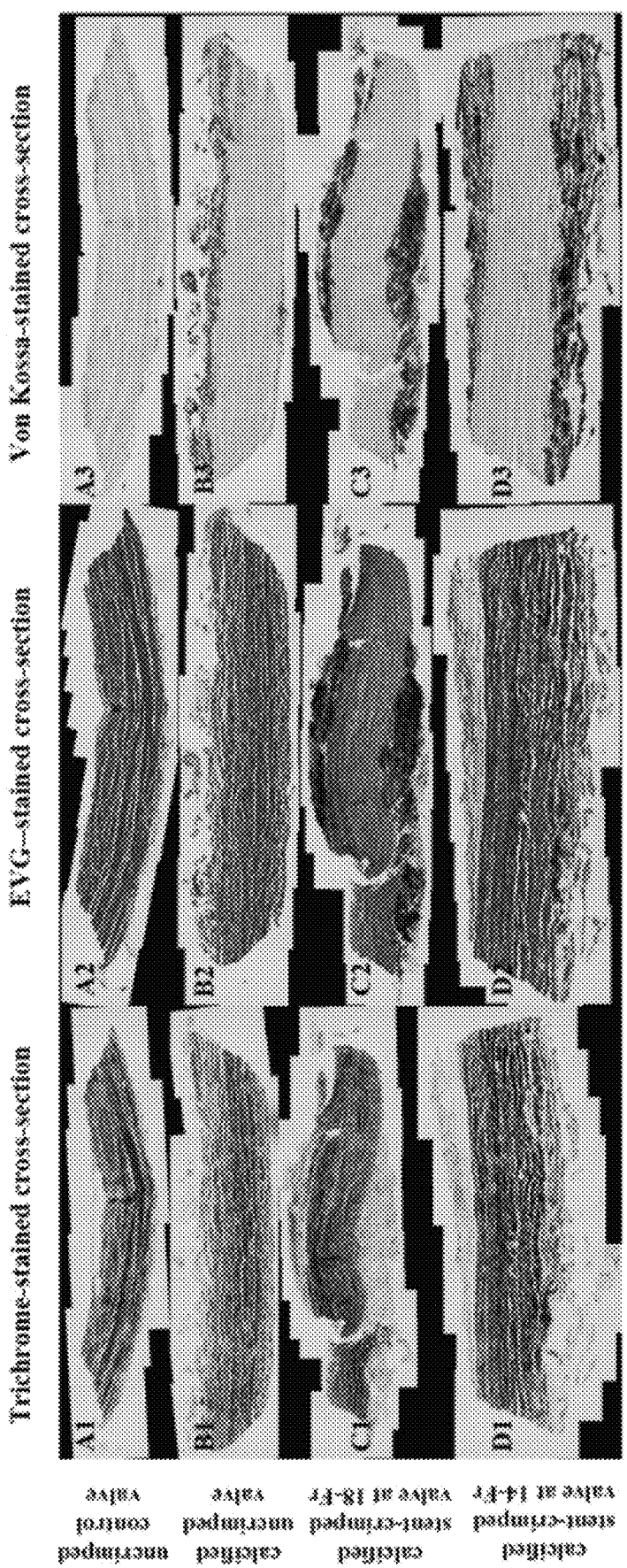

FIG. 13. Association between the leaflet's extracellular matrix degeneration, elastin degradation and calcification. Trichrome (A1-D1), Elastic tissue fibers-Verhoeff-van Gieson (A2-D2) and Von Kossa staining (A3-D3) of the representative samples from each of the 4 studied groups: an uncrimped control valve (A1-A3); a calcified uncrimped valve (B1-B3); a calcified stent-crimped valve at 18-Fr; and (C1-C3) a calcified stent-crimped valve at 14-Fr (D1-D3). EVG: Elastic tissue fibers—Verhoeff's van Gieson.

Figure 14:
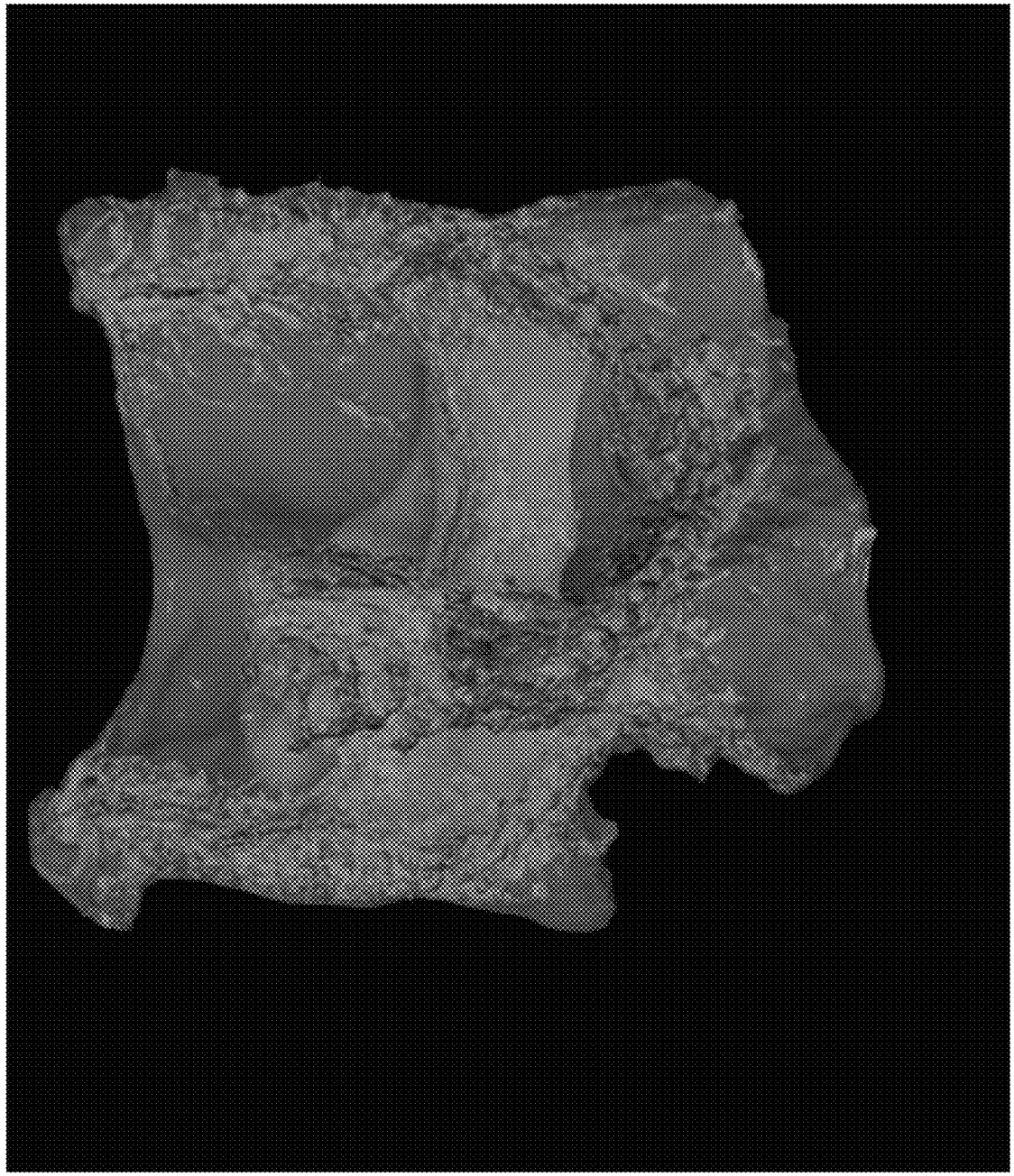

FIG. 14. Maximal calcification is observed in 14-Fr stent-crimp heart valves.

DESCRIPTION

We introduce a method to detect the calcified regions in panoramic images captured from pericardial tissue cross-sections imaged by computed tomography (CT) imaging or stained by calcification-specific dyes, e.g., VON KOSSA staining. The method may be carried out automatically, for example by using computer software written using MATLAB and performed on panoramic images constructed with Fiji software. The purpose of the method is to detect and specify calcified regions in images, and to calculate the amount of calcification. The method is very useful to detect and quantify the calcified regions in complex CT images or in histological images and automates the process of CT or histological image analyses.

We use two software programs to develop our method: 1) Fiji, 2) MATLAB. The Fiji software was used to generate panoramic images. The MATLAB was used to perform our algorithm on the panoramic images and detect the calcified regions in the images.

Our method provides an easy, automated technique for users to detect the calcified regions in tissue cross sections obtained by CT imaging or stained by calcification-specific staining such as but not limited to VON KOSSA. The methods are applied to images captured by CT imaging or obtained from tissue cross-sections stained for calcification. The method may generate a new dual color image to detect the calcified and non-calcified regions in the images.

To the best of our knowledge, there has not been any software developed for the quantification of tissue calcification, based on image processing.

Example 1

Method for Identification and Quantification of Tissue Calcification

Here, we introduce a method to identify and quantify the calcified regions of a tissue stained by a calcification-specific staining such as but not limited to VON KOSSA, and captured under microscope. The method can calculate the amount of the calcification in terms of percentage (Calcification Ratio) with respect to the whole tissue cross-section. Further, the method generates a processed digital image from the tissue cross-sections in two colors (a dual-color image) to visually illustrate the calcified and uncalcified regions.

Figure 1:
FIG. 1: (A) Shows a partial image captured from the portion of the pericardial tissue cross section stained by VON KOSSA. (B) Displays a panoramic image constructed with the 41 partial images using the Fiji software. The dashed box highlights the location of one of the 41 small images in the panoramic image.

The method splits into multi-steps. Here, we explain the method in 5 steps:

1—Build a Panoramic Image from a Tissue Cross-Section Stained by VON KOSSA:

The tissue of interest would be sectioned and stained for a calcification staining such as VON KOSSA. The stained tissue cross-section is mounted on a light microscope stage equipped with a color camera and high magnified objectives. The whole tissue is imaged using a color camera, a high magnified objective and a manual microscope stage. All partial images captured from the tissue cross-section are saved in a folder. The saved partial images are then stitched together such as but not limited by using the Fiji software. Then a panoramic image (a large image) would be constructed from the partial images captured from the tissue cross-section stained by VON KOSSA. For example, we used the Fiji software, the plugin (Stitching/Deprecated/Stitch Multiple Series or Tile Scan File) to construct the panoramic image. FIG. 1 (B) shows a panoramic image of a calcified pericardial tissue previously used as a heart valve leaflet. This image was built by combining 41 partial images. FIG. 1 (A) is one of the 41 partial images used to construct the panoramic image.

2—Quantify the RGB Values of Each Pixel in the Large Image

Each panoramic image is reformatted to an 8-bit image and saved as a Tag Image File Format (TIFF). The final image is imported into a processing software such as but not limited to MATLAB. Each pixel of the image is quantified based on R (Red), G (Green) and B (Blue) values and the location of the pixel in the image. For example, in MATLAB, the command "imtool" can be used to identify the RGB values for each pixel. FIG. 2 displays the process of the panoramic image be quantified. FIG. 2 (A), (B), (C) and (D) show the original panoramic image, the 8-bit image, the calcified region in the 8-bit image (highlighted with a box in FIG. 2 (B)) and the quantified image with RGB values (highlighted with a box in FIG. 2 (C)), respectively.

3—Detect the Pixels Locating in the Calcified Regions

Each pixel in the image is quantified using a code written in MATLAB. All RGB values are overlaid on the image and saved in the code (FIG. 2 (D)). This procedure is repeated for all the panoramic images with different calcification patterns. Based on all RGB values extracted and collected from all panoramic images, the range of RGB values for the calcified and uncalcified pixels is specified and defined for the next step.

Figure 3:
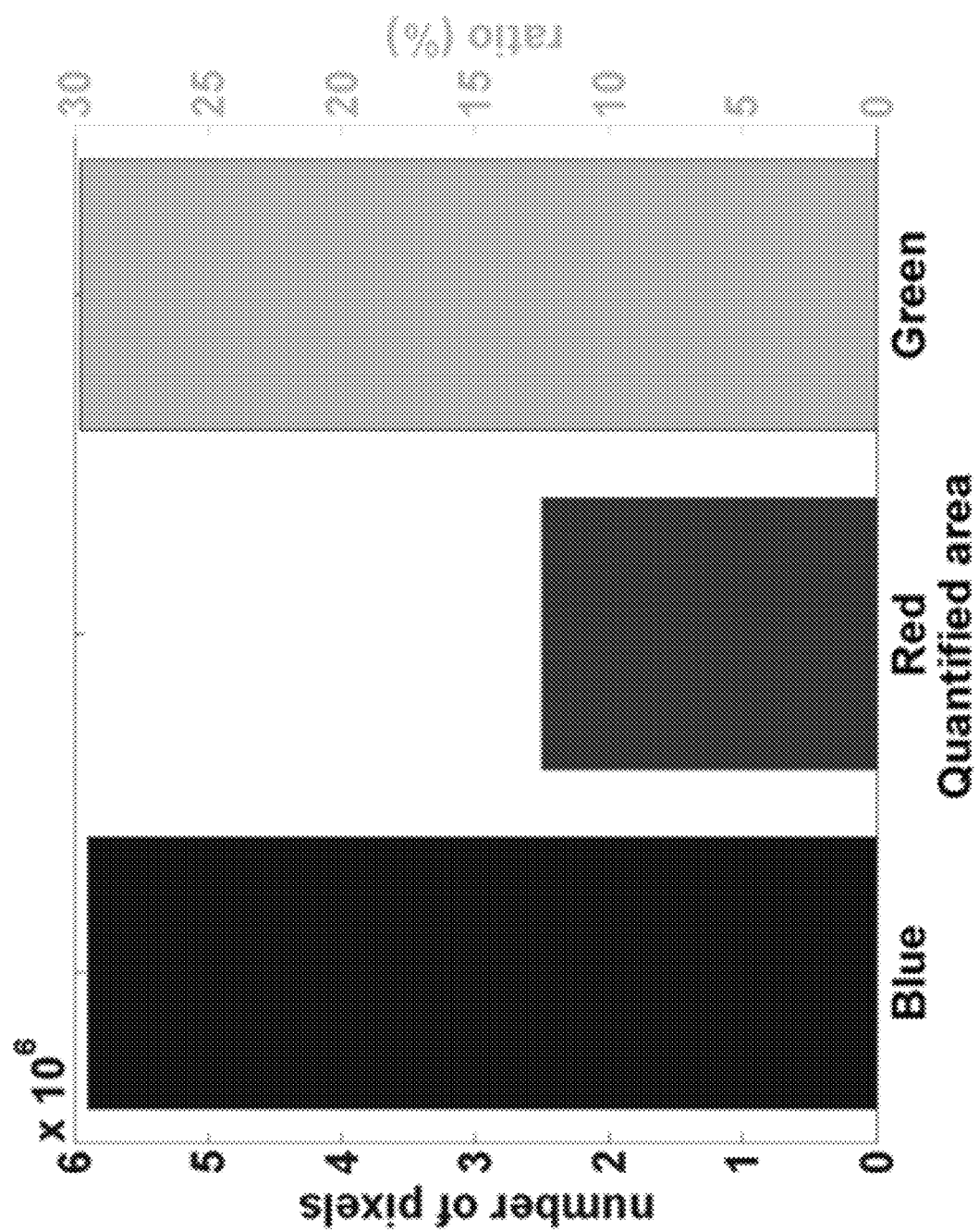
FIG. 3. Shows the final result of the quantified panoramic image shown in FIG. 2. The total pixels of uncalcified and calcified regions are plotted as "Blue" and "Red Quantified area", respectively. The calcification ratio in terms of percentage respect to the whole image ("Green") is calculated based on the following.

4—Compute the Total Pixels of the Calcified and Uncalcified Regions and the Calcification Ratio In this step, based on the range of RGB values specified in the step 3, all calcified and uncalcified regions are distinguished in the all panoramic images. The total number of pixels for the calcified and uncalcified regions for each panoramic image are counted and saved in the code. The total pixels of calcified and uncalcified regions, and the calcification ratio in terms of percentage are then plotted and saved as shown in FIG. 3.

5—Highlight the Calcified and Uncalcified Regions in the Large Image

In the step 4, the pixels of calcified and uncalcified regions are quantified based on the RGB values and assigned to each pixel's location. The quantified pixels for each region are assigned to red and blue colors to generate a new two-color image (a dual color image). The blue and red colors in the new image illustrate the uncalcified and calcified regions, respectively. The new dual color image clearly show the location of the calcified regions in the pericardial tissue cross-section.

6—MATLAB Code

As an example, a MATLAB code developed to compute the calcified and uncalcified regions in tissue cross-section stained by VON KOSSA is provided here:

```
cd('C:\Users\KLab\Desktop\images calcification')
imtool('Imag5e_0001.tif')
close all
clear all
red = 0 ;
blue = 0 ;
black = 0 ;
green = 0 ;
percent = 0 ;
cd('C:\Users\KLab\Desktop\images calcification')
for m=2:2
fname=sprintf('image_%04d.tif',m-1);
I = imread(fname,'tif');
[a,b]=size(I(:,:,1));
F = zeros (a,b);
for i=1:a
for j=1:b
if I(i,j,1)<= 90 && I(i,j,1)>= 20
I(i,j,1)= 255 ;
I(i,j,2)= 0 ;
I(i,j,3)= 0 ;
red=red+1 ;
elseif I(i,j,1)<= 180 && I(i,j,1)>= 95
I(i,j,1)= 0 ;
I(i,j,2)= 0 ;
I(i,j,3)= 255 ;
blue=blue+1 ;
else
I(i,j,1)= 0 ;
I(i,j,2)= 0 ;
I(i,j,3)= 0 ;
black=black+1 ;
F (i,j)=1 ;
end
end
end
filename=sprintf('%04d_analyzied image.tif',m-1);
newFig1 = figure;
set(gca,'LooseInset',get(gca,'TightInset'))
image(I)
daspect([1 1 1]);
axis off
saveas(newFig1, filename);
filename=sprintf('%04d_plot.tif',m-1);
newFig2 = figure;
green= (red/(blue+red))*100 ;
a = [ 1,2,3];
pixels = [blue,red, 0];
ratio = [ 0, 0, green ];
[h,q,p] = plotyy(a,pixels,a ,ratio,'bar','bar');
set(q(1),'facecolor','blue')
set(p,'facecolor','green')
set(h(1), 'YColor', 'blue')
set(h(2), 'YColor', 'green')
set(h(1),'Fontsize', 20, 'FontWeight','bold');
set(h(2),'FontSize', 20, 'FontWeight','bold');
set(gca,'xticklabel',{'Blue','Red','Green'},'FontSize',20,'FontWeight','bold')
set(h(2),'XTick', [ ]);
xlabel('Quantified area','FontSize',20,'FontWeight','bold','Color','black')
ylabel(h(1),'number of pixels') % left y-axis
ylabel(h(2),'ratio (%)') % right y-axis
saveas(newFig2,filename);
```

```
filename=sprintf('%04d_mydata.xlsx',m-1);
L = {'Blue','Red','Green';blue , red , green};
xlswrite(filename, L );
end
```

Example 2

Effect of Stent Crimping on Calcification of Transcatheter Aortic Valves

In this study, we tested whether stent crimping increases the risk for early calcification of a transcatheter aortic valve implant. We found that stent-crimping damage is associated with a higher level of passive leaflet calcification. The association between stent crimping and calcification provides an explanation for premature valve degeneration after a transcatheter aortic valve implant (2019 *Interact Cardiovasc Thorac Surg.* 29(1): 64-73).

OBJECTIVES: Although many challenges related to the acute implantation of transcatheter aortic valves have been resolved, durability and early degeneration are currently the main concerns. Recent reports indicate the potential for early valve degeneration and calcification. However, only little is known about the underlying mechanisms behind the early degeneration of these valves. The goal of this study was to test whether stent crimping increases the risk for early calcification.

METHODS: Stented valves that were crimped at 18-Fr and 14-Fr catheter and uncrimped controls were exposed to a standard calcifying solution for 50 million cycles in an accelerated wear test system. Subsequently, the leaflets of the valves were imaged by microcomputed tomography (micro-CT) followed by histochemical staining and microscopic analyses to quantify calcification and other changes in the leaflets' characteristics.

RESULTS: Heavily calcified regions were found over the stent-crimped leaflets compared to uncrimped controls, particularly around the stent's struts. Micro-CT studies measured the total volume of calcification in the uncrimped valves as $77.31 \pm 1.63$ mm$^3$ vs $95.32 \pm 5.20$ mm$^3$ in 18-Fr and $110.01 \pm 8.33$ mm$^3$ in 14-Fr stent-crimped valves, respectively. These results were congruent with the increase in leaflet thickness measured by CT scans ($0.44 \pm 0.07$ mm in uncrimped valves vs $0.69 \pm 0.15$ mm and $0.75 \pm 0.09$ mm in 18-Fr and 14-Fr stent-crimped valves, respectively). Histological studies confirmed the micro-CT results, denoting that the percentage of calcification in uncrimped leaflets at the valve's posts was $5.34 \pm 3.97$ compared to $19.97 \pm 6.18$ and $27.64 \pm 13.17$ in the 18-Fr and 14-Fr stent-crimped leaflets, respectively.

CONCLUSIONS: This study concludes that stent-crimping damage is associated with a higher level of passive leaflet calcification, which may contribute to early valve degeneration.

Materials and Methods

Seven 25-mm self-expandable heart valves were developed, each having a nitinol stent with leaflets made of clinical-quality bovine pericardial tissue (XenoSure Biologic Patch, LeMaitre Vascular, Burlington, Mass., USA). The durability experiment was performed using a standard accelerated wear test (AWT) system (HiCycle Durability Tester, ViVitro Inc., Victoria, BC, Canada) that can accommodate up to 6 heart valves. Among the 7 valves, 4 were crimped and held at 18-Fr (n=2) and 14-Fr (n=2) for 5 min with the valves' leaflets inside the stent; 2 valves were kept uncrimped and used as the control for the AWT in the presence of the calcifying solution, as described by Barannyk et al. (Barannyk 0 et al. J Biol Phys 2017; 43:279-96). The last valve was kept intact as a control for imaging and histological studies. Testing in the presence of a calcifying solution is the industry standard to determine the calcification potential of the heart valves and shows the tendency of the valves to passive calcification (Kapolos J. et al. J Biomed Mater Res 1997; 38:183-90; and Kriegs M. et al. Int J Artif Organs 2009; 32:794-801) (FIG. 6).

Crimping the Stented Aortic Valves

The transcatheter aortic valves were divided into 4 different groups: group 0 (control uncrimped, N=1), group 1 (uncrimped calcified, N=2), group 2 (crimped at 18-Fr calcified, N=2) and group 3 (crimped at 14-Fr and calcified, N=2). The valves in groups 0 and 1 remained uncrimped, and valves in groups 2 and 3 were crimped at 18-Fr and 14-Fr, respectively. A standard valve crimper was used to crimp the valves in groups 2 and 3. Prior to crimping, all valves in groups 2 and 3 were first immersed in warm water (~37° C.) for 30 min to attain the nitinol stent's full diameter. Finally, all 6 valves in groups 1-3 were placed in saline and shipped to ViVitro Labs for AWT.

50-Million Cycle Accelerated Wear Test

All 6 valves in groups 1-3 were placed in silicone test fixtures with an inner diameter of 24 mm. These fixtures were fabricated from GI-1040 silicone (Silicones, Inc., High Point, N.C., USA) and had a durometer of Shore A 40. This hardness was selected to match the tissue properties of a calcified aortic annulus. To prevent paravalvular leakage and ensure that the valves did not migrate during the test, Dow Corning 734 Flowable RTV silicone was injected around the perimeter of the transcatheter valve to seal the perimeter to the silicone test fixture. The valves mounted in test fixtures were then placed into the ViVitro Labs' HiCycle for AWT. The valves were immersed in a calcification solution, consisting of KCl (55 mM), CaCl$_2$) (1.5 mM), KH$_2$PO$_4$ (1.25 mM) and barbital buffer (20 mM), which was maintained at 37° C. for the duration of the test, as described previously (Barannyk 0 et al. J Biol Phys 2017; 43:279-96). Full opening and closure of the valves were achieved at 1000 cycles per minute. The peak differential pressure during the valve closure was maintained at 100 mmHg, in accordance with the aortic valve normotensive conditions defined in ISO 5840-3:2013. Testing was conducted for 50 million cycles, or nearly 34 days. This duration is equivalent to almost 15 months in a native heart. During the testing, the calcification solution was changed weekly to ensure adequate concentration of Ca$^{++}$ and HPO$_4$. The concentration of calcium and phosphate was 1.2 times more than that in a normal healthy individual (1.57 mmol$^2$/l$^2$) and lower than high-risk level (2.24 mmol$^2$/l$^2$) in blood (Barannyk 0 et al. J Biol Phys 2017; 43:279-96; and Tertti R. et al. Hemodialysis Int 2007; 11:411-16). The pH of the solution was measured at each fluid change and kept in a range between 7.37 and 7.46. The valves were shipped back to the University of California, Irvine in saline immediately after completion of the test for further analyses.

Quantifying the Calcification by Microcomputed Tomographic Scanning

All 7 valves were sent to PerkinElmer, Inc. to be imaged using a microcomputed tomography (micro-CT) system (Quantum GX2; PerkinElmer, Hopkinton, Mass., USA). A similar acquisition setting was used for scanning all the valves: 90 KV, 88 µA; field of view: 36 mm; acquisition time: 14 min; camera mode: high resolution. A sub-volume reconstruction of the original images with a field of view of 10 mm and a voxel size of 20 µm was performed to obtain higher resolution data of the valves' leaflets to detect and quantify calcification. All 7 valves were imaged from top to bottom (z-stack imaging) with and without their nitinol stents. All images were imported into VivoQuant 3.0 software (Invicro LLC, Boston, Mass., USA) to quantify and distinguish the sutures and calcification regions, respectively.

Quantifying the Valve Thickness

The transverse view (top view) of all the valves (groups 0-3) were imported into the VivoQuant software. The leaflet of each valve was measured adjacent to the valve's posts and at the centre of the leaflet's belly. In total, the leaflet thickness was measured at 9 positions for each valve.

Quantifying the Calcification by Histological Analyses

To validate the CT scan analyses after completion of the imaging studies, the valves' leaflets were carefully detached from the stents for histological analyses. Three tissue cross-sections (3 mm diameter) were collected from each valve's posts near the stent using a biopsy punch (3 specimens for each valve). All specimens were stored in saline and shipped to North Bay Histology Lab (Novato, Calif., USA) for analyses. Each sample was individually embedded, sectioned and stained for calcium characterization (Von Kossa stain), elastin composition (Verhoeff-van Gieson stain) and collagen fibre quantification (trichrome III and haematoxylin and eosin stains). The stained samples were visualized using a light microscope and stored as digital computer images for further analyses. From each stained sample, more than 10 images were captured and stitched together to reconstruct the complete field of view of the tissue cross-section.

The images acquired from the Von Kossa-stained sample were imported into a computer, and an in-house MATLAB (MathWorks, Inc., Natick, Mass., USA) routine was used to analyse the data. The total pixels for each image were first calculated and quantified in red, green and blue values, and the calcified and uncalcified pixels were assigned to red and blue values in reconstructed images, respectively. Finally, the ratio of calcified pixels with respect to the total pixels (the total calcified and uncalcified pixels) in terms of percentage was calculated and plotted.

Statistical Analysis

All the data quantified from the micro-CT scan and histological samples are presented as mean±standard deviation. Because only 6 valves could be loaded for each AWT experiment, the number of our samples for each study group was small. Therefore, to analyze the data, each study group was compared using a non-parametric test (Mann-Whitney U-test) (Mann H B et al. Ann Math Statist 1947; 18: 50-60). The $U_{Critical}$ for each pairwise comparison was determined from the Mann-Whitney U-test table (2-tailed testing) based on a 2-sided level of significance (a=0.05). The minimum of the calculated U for each pairwise comparison was compared to the $U_{Critical}$. Based on the Mann-Whitney U-test, if the minimum calculated U was less than or equal to the $U_{Critical}$, the null hypothesis (indistinguishable trait in 2 studied groups) was rejected in favor of the research hypothesis (distinct trait in 2 studied groups). If the U was greater than the $U_{Critical}$, the null hypotheses could not be rejected; thus, there was no difference between the 2 studied groups. Due to the small sample size in this study, we only report the U values and compare the $U_{Minimum}$ to $U_{Critical}$ for each studied group.

Results

Microcomputed Tomographic Imaging Results

Quantification of Valve Calcification.

The leaflet calcification is compared among the different groups in FIG. 7. The sutures and calcification regions are distinguished by dark gray and light gray, respectively. FIG. 8, (C) and (D) compare the total measured calcification among the studied groups. The total volume of calcification in the uncrimped valves was 77.31±1.63 mm$^3$ vs 95.32±5.20 mm$^3$ for 18-Fr and 110.01±8.33 mm$^3$ for 14-Fr stent-crimped, respectively. Based on the pairwise non-parametric analyses, the volume of calcification in the uncrimped valves (N=2) was less than that in the crimped valves at 18-Fr (N=2) and at 14-Fr (N=2); as well, this quantity was different between both crimped groups (Mann-Whitney $U_{Minimum}=0$, $n_2=n_3=n_4=2$).

Any increase to the suture volume beyond the baseline value after the 50-million cycle test was attributed to the deposition of calcium over the sutures. However, since calcification around the sutures is not related to our hypothesis considering the effect of calcium deposition in the leaflet. Nevertheless, these changes in the volume of the sutures are reported in FIG. 8 (B). The volume of the baseline sutures in the control uncrimped valve was 20.38 mm$^3$ (N=1), whereas the total volume of the sutures had increased to 47.28±0.44 mm$^3$ (N=2), 43.96±6.94 mm$^3$ (N=2) and 42.88±4.17 mm$^3$ (N=2) for uncrimped, 18-Fr and 14-Fr crimped valves, respectively (FIG. 8 (B)). According to the non-parametric analyses, the total volume of sutures in group 0 was different than that in groups 1-3 (Mann-Whitney $U_{Minimum}=0$, $n_1=1$, $n_{2,3,4}=6$). This finding suggests that calcium deposition occurs around the sutures in valves exposed to a calcifying solution, regardless of stent crimping.

Quantification of Leaflet Thickness.

Following 50 million cycles of AWT, the thickness of the valve leaflets was measured at 9 different locations, as discussed previously (FIG. 9). The average thickness of the uncrimped control leaflets was 0.30±0.04 mm, whereas the average thickness of the uncrimped/calcified and stent-crimped leaflets at 18-Fr and 14-Fr was 0.44±0.07 mm, 0.75±0.09 mm and 0.69±0.15 mm, respectively. FIG. 10 (B) shows a comparison of the leaflet thickness among the studied groups. The average thickness of the uncrimped control leaflets differed from that of uncrimped/calcified leaflets (Mann-Whitney $U_{Minimum}=5<U_{Critical}=42$, $n_1=9$, $n_2=18$). As well, the average thickness of the uncrimped/calcified leaflets differed from that of the stent-crimped leaflets at 18-Fr (Mann-Whitney $U_{Minimum}=2<U_{Critical}=99$, $n_2=18$, $n_3=18$) and to stent-crimped leaflets at 14-Fr (Mann-Whitney $U_{Minimum}=25<U_{Critical}=99$, $n_2=18$, $n_4=18$). Nevertheless, the average thickness of the stent-crimped leaflets at 18-Fr did not differ from that of the 14-Fr (Mann-Whitney $U_{Minimum}=125>U_{Critical}=99$, $n_3=18$, $n_4=18$).

Histological Results

FIG. 11 (A1) shows the Von Kossa staining of a control uncalcified/uncrimped leaflet with cells and cytoplasm in light gray without any calcified regions. FIG. 11, (B1-D1) represent Von Kossa staining of the calcified valves. The calcified regions are clearly detectable in the images as black regions (FIG. 11, (B1-D1)), and the top and bottom tissue layers were calcified and degenerated compared to the leaflet tissue core. The uncrimped valves showed calcification in the superficial layers of their leaflets (FIG. 11, (B1)), whereas the stent-crimped valves were deeply calcified at both the ventricular and aortic sides of the leaflets (FIGS. 11 (C1 and D1)). Subsequently, the calcified regions were quantified and measured by an in-house MATLAB code that detects and counts the pixels stained by Von Kossa. The ratio of the calcification to the whole tissue cross-section (expressed in terms of percentage) was calculated for each valve's posts and then averaged for each study group (FIG. 12 (A and B)). The data indicate that the uncrimped leaflets showed an average calcification of 5.34±3.97% vs the stent-crimped leaflets, which had an average calcification of 19.97±6.18% and 27.64±13.17% at 18-Fr and 14-Fr stent crimping, respectively. The non-parametric test shows that the average calcification of the uncrimped/calcified valve compared to that of the crimped/calcified valves at 18-Fr (Mann-Whitney $U_{Minimum}=0<U_{Critical}=5$, $n_2=6$, $n_3=6$) or between the uncrimped/calcified valves and the crimped/calcified valves at 14-Fr differed (Mann-Whitney $U_{Minimum}=0<U_{Critical}=5$, $n_2=6$, $n_4=6$). No difference was observed between the valves crimped at 18-Fr and 14-Fr (Mann-Whitney $U_{Minimum}=12>U_{Critical}=5$, $n_3=6$, $n_4=6$).

FIG. 13 presents the tissue cross-sections from each valve's post, stained with trichrome, Verhoeff-van Gieson and hematoxylin and eosin. FIG. 13 shows the staining of control, uncrimped, 18-Fr and 14-Fr stent-crimped valves, respectively. The cross-sections of the uncrimped leaflets show the normal structure of the cells and the extracellular matrix (ECM) (FIG. 13 (A1-3)) with elastin and collagen fibers in light gray and dark gray staining, respectively (FIG. 13 (A1-3)). FIGS. 12 (B1-3, C1-3 and D1-3) demonstrate that the ECM of the calcified tissue possesses a different structure in all the studied valves, which is more pronounced at the calcified regions. The superficial layers of the leaflets show the effect of calcification on the ECM, whereas the core of the leaflets remained intact. Based on trichrome and hematoxylin and eosin staining, the calcification led to degeneration of collagen and elastin fibers at the superficial layers of the calcified heart valves. In uncrimped valves, collagen and elastin fibers were degraded only at the superficial layers of the leaflets (FIG. 13 (B1-3)), whereas in both groups of stent-crimped valves, collagen and elastin fibers were degenerated on both the aortic and ventricular sides of the leaflets (FIGS. 13 (C1-3 and D1-3)). In these valves, degradation of the collagen and elastin advanced to the deeper tissue layers of the leaflets. FIGS. 11 (C1-D1) show that the calcified regions evolved from the superficial layers towards the tissue core.

Discussion

The consensus among the experts is that the durability of surgical bioprosthetic and transcatheter valves may differ because in transcatheter valves, the leaflets mounted within the stent are prone to microscopic damage due to stent crimping (Dvir D et al. Circulation 2018; 137:388). In the early days of TAVR, the main focus was on the short-term procedural success. Nevertheless, the durability of the valve's leaflets becomes more relevant because TAVR is being offered to younger and lower risk patients. These patients are expected to survive much longer than those who received TAVR in the early days. Thus, improving durability of the valve is of significant importance. We have addressed whether stent crimping of the valve leaflets is responsible for structural valve degeneration after 50 million cycles (equivalent to 15 months in the human heart) of exposure to a standard calcifying solution.

Association of Stent Crimping with Leaflet Thickening and Calcification

As validated by histological analysis, our micro-CT data show that calcification is more prominent in the regions around the valve sutures and at the valves' posts (FIG. 7), which are under high mechanical stress. Stented valves crimped at 18-Fr and 14-Fr (FIG. 8 (D)) exhibited more calcification than the uncrimped valves; however, the difference between the 2 stent-crimped valve groups was not noticeable, denoting that more aggressive crimping than 18-Fr may not lead to further passive calcification. However, because it was previously shown that more aggressive stent crimping is associated with deeper tissue damage (Alavi S H et al. Ann Thorac Surg 2014; 97:1260-6), the new results should be considered with caution, and further validation with a large cohort of valves may be needed to confirm them. Furthermore, we found that the crimped leaflets (FIG. 10 (B)) were thicker than the uncrimped leaflets after 50 million cycles of exposure to a calcifying solution. This observation is interesting and, in our opinion, is associated with excessive calcium deposition in microscopic defects over the leaflets' ECM, which later on appears as calcification and structural valve degeneration (Dvir D et al. Circulation 2018; 137:388; Otto C M. et al. Heart 2002; 88:321-2; Cheng C L et al. J Mech Behav Biomed Mater 2017; 74:324-32; and Foroutan F. et al. Heart 2017; 103:1899).

Stent-Crimp-Induced Damage to the Extracellular Matrix and Calcium Depositions in the Leaflets Our histological results (FIGS. 11 and 13) suggest that calcium deposits were higher around the sutures and valve posts for all the studied valves. These regions in a valve are usually under higher mechanical stress, and the ECM of these regions is therefore more prone to disruption (Alavi S H et al. Ann Thorac Surg 2014; 97:1260-6), which may lead to calcification and early structural valve degeneration. We hypothesized that once the valve experiences stent crimping, the thin struts of the stent, with their very small surface area, amplify the crimping force into an enormous normal stress applied to the leaflets (like a cutting knife). This stress, which represents the external crimping force acting over the cross-sectional area of the leaflet, results in microscopic damage to the collagen fibers and elastin of the leaflets, as shown previously (Dasi L P. et al. Ann Biomed Eng 2017; 45:310-31). This stress may be responsible for remodeling the elastin and collagen fibers of the ECM of the leaflets (Delogne C. et al. J Microsc 2007; 228:62-77), which may increase the aggregation and deposition of calcium in the tissue (Schoen F J et al. Am J Pathol 1986; 123:134-45; Bertazzo S. et al. Nature Mater 2013; 12: 576-83; and Schoen F J et al. Ann Thorac Surg 2005; 79: 1072-80). FIGS. 11 and 13 illustrate the crimp-induced damage to the elastin and collagen fibrils of the leaflets. Other studies have also reported the damaging effects of stent crimping on valve leaflets (Zegdi R et al. Eur J Cardiothorac Surg 2011; 40:257-60; Kiefer P et al. Ann Thorac Surg 2011; 92:155-60; and Khoffi F. et al. J Biomed Mater Res B Res 2015; 103:1488-97). Our durability data corroborate those of previous studies, indicating that stent crimping may damage the ECM of the leaflets (Zegdi R et al. Eur J Cardiothorac Surg 2011; 40:257-60; Kiefer P et al. Ann Thorac Surg 2011; 92:155-60; Dasi L P. et al. Ann Biomed Eng 2017; 45:310-31; and Khoffi F. et al. J Biomed Mater Res B Res 2015; 103:1488-97) and show for the first time that stent-crimped valves may be prone to further passive calcium deposits on their leaflets.

Accordingly, our observations showed that, in the uncrimped valves, only superficial layers of the leaflets were calcified. Nevertheless, in both 18-Fr and 14-Fr stent-crimped valves, the calcification penetrated the deeper layers of the tissue, which led to more calcium deposits compared to the uncrimped valves. Stent-crimp-induced damage to the ECM may allow calcium to penetrate more profoundly from the superficial layers down to the deeper layers (FIGS. 11 and 13). The influx of calcium into structurally damaged regions can result in calcium crystallization and lead to the potential growth of the microcalcification regions into clinically apparent calcium nodules on the leaflet.

Because the standard AWT systems can accommodate only 6 valves at a time, the number of tested valves in this study was low. Therefore, we emphasize the potential association between 2 observations, namely, stent crimping and the occurrence of calcification. Furthermore, the calcification reported in this study is passive and does not reflect the active, cellular-based calcification phenomenon that is present in the human heart. However, passive calcification tests are considered standard in heart valve research and development and are commonly used to test the tendency of a valve to become calcified (Arora S et al. Cardiovasc Diagn Ther 2017; 7:1-3; and Barannyk O et al. J Biol Phys 2017; 43:279-96).

CONCLUSION

We conclude that more prominent calcified regions and damage to the ECM are observed near the posts of the stent-crimped valves compared to the uncrimped controls. Accordingly, the data suggest a potential association between stent crimping and calcification, which may explain the durability concerns associated with transcatheter aortic valves. Reduced durability and the potential for early degeneration are current concerns for the long-term treatment of patients with aortic valve disease. An understanding of the effect of stent crimping provides a basis to improve the durability of transcatheter heart valves.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method of identifying and quantifying calcified regions of a tissue comprising obtaining an image of a cross-section of the tissue, wherein the image distinguishes between calcified regions and non-calcified regions of the cross-section of the tissue and wherein calculating a calcification ratio is based on the following formula:

$$\text{Calcification Ratio} = \frac{\text{total pixels of the calcified region}}{\text{total pixels of the calcified and uncalcified regions}} \times (100).$$

2. The method according to claim 1, comprising using computed tomography (CT) to obtain the image of the cross-section of the tissue, wherein calcified regions in the tissue are distinguished by appearance of high-density material in a CT cross-sectional image.

3. The method according to claim 2, comprising non-invasively obtaining the CT cross-sectional image of the tissue in a living subject.

4. The method according to claim 1, comprising histologically staining the cross section of the tissue by a calcification-specific stain and generating a dual color image to detect calcified and non-calcified regions of the cross-section of the tissue.

5. The method of claim 4, wherein the tissue is stained by von Kossa staining.

6. The method of claim 1, wherein the image is of a native or prosthetic heart valve.

7. The method of claim 6, wherein the native or prosthetic heart valve comprises pericardial tissue.

8. The method of claim 6, wherein the native or prosthetic heart valve comprises xenogeneic heart valve tissue.

9. The method of claim 6 wherein the native or prosthetic heart valve comprises a synthetic polymeric material.

10. The method according to claim 1, wherein a panoramic image is constructed from partial images captured from the tissue.

11. The method according to claim 1, wherein the calcified region is in a subject and wherein the method further comprises treating the subject with a medical procedure to reduce one or more of the calcified regions.

12. A method of detecting a change in size of a calcified region of a tissue over time comprising:
 (a) using the method according to claim 1 to:
  (i) identify and quantify a first size of the calcified region of the tissue at a first time, and
  (ii) identify and quantify a second size of the corresponding calcified region of the tissue at a second time, and
 (b) detecting a change in size between the first and second size of the calcified region of the tissue in the image of a cross-section of the tissue.

13. The method according to claim 12, wherein the calcified region is in a subject and wherein the method further comprises treating the subject with a medical procedure to reduce the calcified tissue if the second size is increased compared to the first size.

14. The method according to claim 12, wherein the calcified region of tissue is part of a transcatheter heart valve implanted in a subject.

15. The method according to claim 14, wherein the calcified region increases thickness of leaflets in the transcatheter heart valve.

16. The method of claim 14, wherein the calcified region produces one or more calcium nodules on a heart valve leaflet.

17. The method according to claim 14, wherein the calcified region is located at valve sutures or at valve posts, which are under high mechanical stress.

18. The method of claim 1, wherein the sizes or ratios of the calcified regions and non-calcified region of the cross-section of the tissue are calculated by a computer software program configured to:
 a. obtain the image of the cross-section of the tissue, comprising constructing a panoramic image from partial images,
 b. quantify RGB values for each pixel in the panoramic image, and
 c. calculate the total pixels of calcified and non-calcified regions and the calcification ratio.

\* \* \* \* \*